(12) United States Patent
Franco et al.

(10) Patent No.: US 9,733,385 B2
(45) Date of Patent: Aug. 15, 2017

(54) SYSTEMS AND METHODS FOR THE AUTOMATIC DETECTION OF LITHIUM BATTERIES IN CARGO, BAGGAGE, PARCELS, AND OTHER CONTAINERS

(71) Applicant: Rapiscan Systems, Inc., Torrance, CA (US)

(72) Inventors: Ed Franco, San Mateo, CA (US); Ling Tang, Newton, MA (US); Jing Ye Shea, Groveland, MA (US); Minyang Huang, Andover, MA (US); Jolyon Browne, San Jose, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 172 days.

(21) Appl. No.: 14/800,595

(22) Filed: Jul. 15, 2015

(65) Prior Publication Data
US 2016/0084984 A1    Mar. 24, 2016

Related U.S. Application Data

(60) Provisional application No. 62/024,844, filed on Jul. 15, 2014.

(51) Int. Cl.
*G01N 23/04*    (2006.01)
*G01V 5/00*    (2006.01)

(52) U.S. Cl.
CPC .......... *G01V 5/0041* (2013.01); *G01N 23/04* (2013.01)

(58) Field of Classification Search
CPC ...... G01V 5/00; G01V 5/0008; G01V 5/0016; G01V 5/0041; G01N 23/00; G01N 23/02; G01N 23/04; G01N 23/08; G01N 23/083; G01N 23/087; G01N 23/10; G06T 2207/10116
USPC ..................................... 378/57, 62; 382/132
See application file for complete search history.

(56) References Cited

U.S. PATENT DOCUMENTS

| | | | |
|---|---|---|---|
| 5,600,303 | A | 2/1997 | Husseiny et al. |
| 7,702,069 | B2 | 4/2010 | Panesar et al. |
| 7,928,400 | B1 | 4/2011 | Diawara et al. |
| 8,213,570 | B2 | 7/2012 | Panesar et al. |
| 9,310,322 | B2 | 4/2016 | Panesar et al. |
| 2003/0068557 | A1 | 4/2003 | Kumashiro et al. |
| 2008/0170670 | A1 | 7/2008 | Bhatt et al. |
| 2010/0295689 | A1 | 11/2010 | Armistead, Jr. et al. |
| 2011/0235777 | A1 | 9/2011 | Gozani et al. |

FOREIGN PATENT DOCUMENTS

WO    2016011205    1/2016

OTHER PUBLICATIONS

International Search Report for PCT/US2015/040653, Dec. 16, 2015.

*Primary Examiner* — Jurie Yun
(74) *Attorney, Agent, or Firm* — Novel IP

(57) ABSTRACT

The present specification discloses methods for scanning objects for the presence of lithium batteries. Normalized transmission X-ray data is used to generate organic, effective Z, and attenuation-based images. These images are then segmented using a combination of thresholding and region growing techniques to identify regions of interest. The regions are classified as lithium batteries or other objects, based on characteristics such as area of the region, its organic intensity, $Z_{eff}$ number, shape, spatial arrangement and texture.

23 Claims, 11 Drawing Sheets

Top View

Side View

Threshold: 145

(B) Top View $Z_{eff}$ Histogram

Threshold: 145

Side View $Z_{eff}$ Histogram (C) Segmented $Z_{eff}$ Image
(Top View)

Segmented $Z_{eff}$ Image
(Side View)

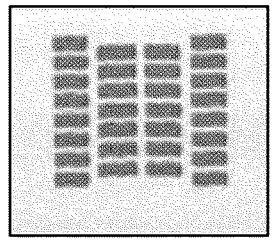 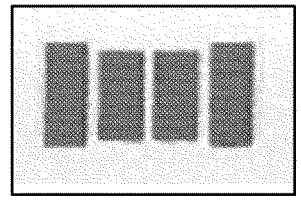
(A) Top View
FIG. 5a
Side View
FIG. 5b
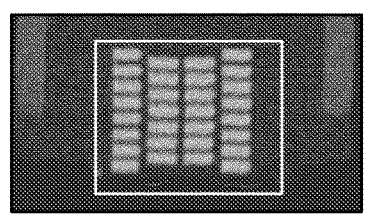 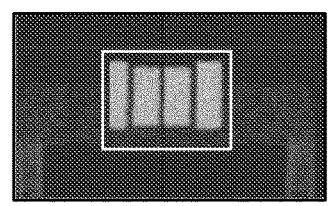
(B) Top View
FIG. 5c
Side View
FIG. 5d
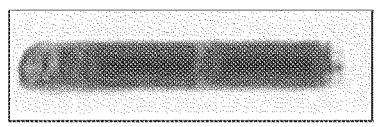 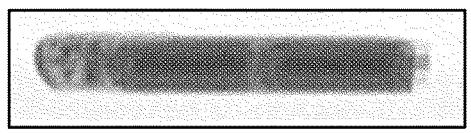
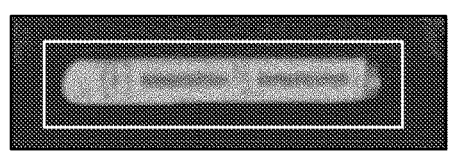 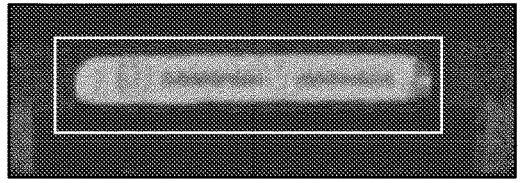
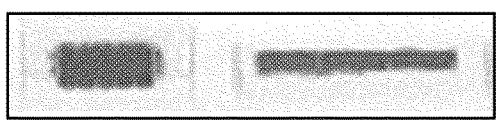 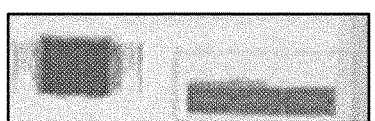
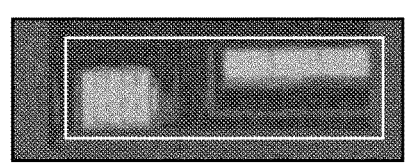 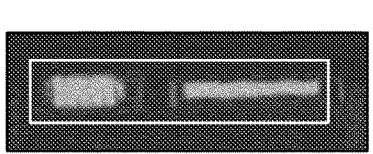
(C) Top View
FIG. 5e
Side View
FIG. 5f X-ray Image (Top View)

X-ray Image (Side View)

Segmented $Z_{eff}$ Image (Top View)

Segmented $Z_{eff}$ Image (Side View)

Organic Seed Map

Segmented Organic Image

SYSTEMS AND METHODS FOR THE AUTOMATIC DETECTION OF LITHIUM BATTERIES IN CARGO, BAGGAGE, PARCELS, AND OTHER CONTAINERS

CROSS-REFERENCE

The present application relies on U.S. Patent Provisional Application No. 62/024,844, filed on Jul. 15, 2014, for priority and is hereby incorporated by reference.

FIELD

The present specification generally relates to the field of radiant energy imaging systems, and more specifically to a system for automatically detecting the presence of lithium batteries in cargo, baggage, parcels and other containers at transit points such as airports.

BACKGROUND

Shipping lithium batteries in air cargo is regulated since the batteries can catch fire if they are improperly packaged, damaged, or improperly designed or assembled. For example, a United Parcel Service (UPS) airplane caught fire in 2010 and crashed on its way to Germany after arriving in Dubai from Hong Kong. The investigation into the crash by the Civil Aviation Authority (CAA) of Dubai identified the improper packaging of the batteries as the cause of the fire that preceded the crash. Because the UPS airplane contained cargo that included lithium batteries, the cargo should have been declared as hazardous.

Non-intrusive inspection systems are presently limited in their ability to detect dangerous or unsafe objects such as lithium batteries concealed in cargo. It is known in the art that images of various types of materials can be generated by using various dual-energy X-ray radiographic techniques. The intensity of transmitted X-rays provides information about the density and average atomic number (Z) of the targeted material. However, this information is not sufficient to identify, with specificity, the materials of interest present inside the target.

As a result of the image modulation based on the densities and atomic numbers of various materials, it is common for X-ray imaging systems to produce images with dark areas. Although these areas might suggest the presence of hazardous materials, they do not yield sufficient information for an operator to decide the exact nature of the imaged materials. Also, radiographs produced by conventional X-ray systems are often difficult to interpret because objects are superimposed. Therefore, a trained operator must study and interpret each image to render an opinion on the presence of a material of interest. Operator fatigue and distraction can compromise detection performance when a large number of images are to be interpreted, such as at high traffic transit points and ports. Even with automated systems, it becomes difficult to comply with the implied requirement to keep the number of false alarms low, when the system is operated at high throughputs.

One method of obtaining more useful information and clarity from X-ray imaging is using dual energy systems to measure the effective atomic numbers of materials passing through luggage, baggage, parcel, and cargo inspection areas. However, the dual energy method does not readily allow for the calculation of the actual atomic number of the concealed object itself, but rather yields only an average atomic number that represents the mix of the various items falling within the X-ray beam path, as the contents under inspection may be composed of different items and are rarely conveniently separated. Thus dual-energy analysis is often confounded.

Thus, X-ray inspection systems currently available in the art provide limited clarity for detection of materials such as lithium batteries. Accordingly, there is still a need for an improved detection system that can perform the complex task of detecting lithium batteries and distinguishing them from other types of batteries that are allowed to be transported without restriction. Such a system needs to be highly specific, so as to reliably discern materials of interest even in containers, baggage, and cargo with high clutter.

SUMMARY

The present specification describes an inspection system for scanning air cargo, baggage for detecting the presence of lithium batteries, comprising, in an embodiment, at least one radiation source; at least one detector array corresponding to at least one radiation source; and, a processing unit comprising at least one processor, memory, and programmatic instructions, wherein, through the operation of the at least one processor, the memory, and the programmatic instructions, said processing unit: obtains transmission X-ray data representative of a generated radiographic image; normalizes said X-ray data to remove effects of dark current and to remove effects of pixel-to-pixel variations; generates at least one of organic image data and effective Z image data from said normalized data; segments said at least one of organic image data and effective Z image data based on an organic density of materials and a threshold effective atomic number ($Z_{eff}$), respectively; identifies at least one region of interest in said at least one of organic image data and effective Z image data based on said segmentation, wherein said at least one region of interest comprises a plurality of characteristics; and classifies said at least one region of interest as containing at least one lithium battery based on the plurality of characteristics of said at least one region of interest.

Optionally, said at least one region of interest is identified in segmented images based on properties such as area, shape, organic thickness, and $Z_{eff}$ number.

Optionally, the plurality of characteristics used by said processing unit to classify the at least one region of interest as containing at least one lithium battery include area, organic intensity, $Z_{eff}$ number, shape, X-ray attenuation level, spatial arrangement and texture of said region.

Optionally, the processing unit classifies said at least one region of interest as containing at least two lithium batteries based on the plurality of characteristics of said at least one region of interest and wherein said plurality of characteristics include a spatial arrangement defined by a first rectangular portion having a $Z_{eff}$ in a range of 14 to 20 and an organic density represented by a pixel map of at least 4000 pixels, a second rectangular portion having a $Z_{eff}$ in a range of 14 to 20 and an organic density represented by a pixel map of at least 4000 pixels, and a gap separating the first rectangular portion and second rectangular portion, said gap having a $Z_{eff}$ of less than 14.

Optionally, the system uses one X-ray source operating at a single voltage.

Still optionally, the system uses two X-ray sources, each operating at a single voltage. In some embodiments, the two X-ray sources may switch between two operating voltages in an interlaced fashion. In some embodiments, a first X-ray source is approximately perpendicular to a second X-ray source. In some embodiments, the inspection system may produce two substantially simultaneous images from the two X-ray sources. Optionally, the two simultaneous images provide a horizontal view and a vertical view of the cargo being scanned.

Optionally, the system uses from three to five X-ray sources, each operating at a single voltage.

Optionally, the detector array comprises dual-energy detectors.

Optionally, said threshold effective atomic number ($Z_{eff}$) separates low-Z and high-Z materials in the effective Z image data.

Optionally, during the segmentation of organic images, the processing unit applies region growing techniques.

In some embodiments, the processing unit may be configured to apply the region growing techniques when scanning cargo, baggage, or parcels with high clutter.

Optionally, the results of a scan are manually verified to fine-tune identification criteria for lithium batteries.

The present specification describes a method for detecting the presence of at least one lithium battery in a target, said method comprising, in one embodiment, obtaining transmission X-ray data representative of a generated radiographic image of the target; normalizing said X-ray data to remove effects of at least one of dark current or pixel-to-pixel variation; generating effective Z images from said normalized data; segmenting said effective Z images based on a threshold effective atomic number ($Z_{eff}$); identifying at least one region of interest in said effective Z images based on said segmentation; and classifying said at least one region of interest as containing said at least one lithium battery based on characteristics of said at least one region of interest, said characteristics include a first substantially rectangular portion having a $Z_{eff}$ in a range of 14 to 20.

Optionally, the processing unit may be configured to identify said at least one region of interest in segmented images based on properties such as area, shape, organic thickness, and $Z_{eff}$ number.

Optionally, the characteristics used for classifying at least one region of interest as containing at least one lithium battery further includes area, organic intensity, X-ray attenuation level, spatial arrangement and texture of said region.

Optionally, the characteristics used for classifying at least one region of interest as containing at least one lithium battery further a first substantially rectangular portion having a $Z_{eff}$ in a range of 14 to 20, a second substantially rectangular portion having a $Z_{eff}$ in a range of 14 to 20 and a gap separating the first substantially rectangular portion and second substantially rectangular portion, said gap having a $Z_{eff}$ of less than 14.

Optionally, an organic density of the first substantially rectangular portion is at least 4000 pixels and an organic density of the second substantially rectangular portion is at least 4000 pixels.

Optionally, the processing unit may be adapted to use the threshold effective atomic number to separate low-Z and high-Z materials in the effective Z images.

In some embodiments, the processing unit may be configured to apply region growing techniques when scanning cargo, baggage, or parcels with high clutter.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 4c illustrates the $Z_{eff}$ histogram corresponding to the image shown in FIG. 4a;

FIG. 5a illustrates top view X-ray and top views of segmented $Z_{eff}$ images for LSH14 Li-metal batteries in accordance with an embodiment of the present specification;

FIG. 5b illustrates side view X-ray and side views of segmented $Z_{eff}$ images for LSH14 Li-metal batteries in accordance with an embodiment of the present specification;

FIG. 5c illustrates top view X-ray and top views of segmented $Z_{eff}$ images for a 50-cycle electric bicycle Li-ion battery in accordance with an embodiment of the present specification;

FIG. 5d illustrates side view X-ray and side views of segmented $Z_{eff}$ images for a 50-cycle electric bicycle Li-ion battery in accordance with an embodiment of the present specification;

FIG. 5e illustrates top view X-ray and top views of segmented $Z_{eff}$ images for a BL1830 power tool Li-ion battery in accordance with an embodiment of the present specification;

FIG. 5f illustrates side view X-ray and side views of segmented $Z_{eff}$ images for a 6-cell laptop Li-ion battery in accordance with an embodiment of the present specification;

DETAILED DESCRIPTION

The present specification describes an improved method for screening luggage and cargo that uses x-ray scanning techniques for detection of materials of interest, specifically lithium batteries as their transportation is regulated due to their flammable content. In an embodiment, the method of present specification enables the generation of images in which areas containing lithium batteries are segregated from areas containing other types of batteries which are not regulated, so that they can be classified as a potential safety threat. In an embodiment, the method of present specification can be implemented with existing cargo scanning systems, commonly deployed at cargo handling facilities that service commercial airlines. It may be appreciated by a person of ordinary skill in the art that the system and method of the present specification can be used for screening of bags, parcels, luggage, containers and cargo at various types of transit points and other commercial applications. In embodiments, the systems and methods of the present specification can be used for screening targets of any size ranging from small parcels to large objects and areas such as containers, trains, airplanes, ships, tunnels etc.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
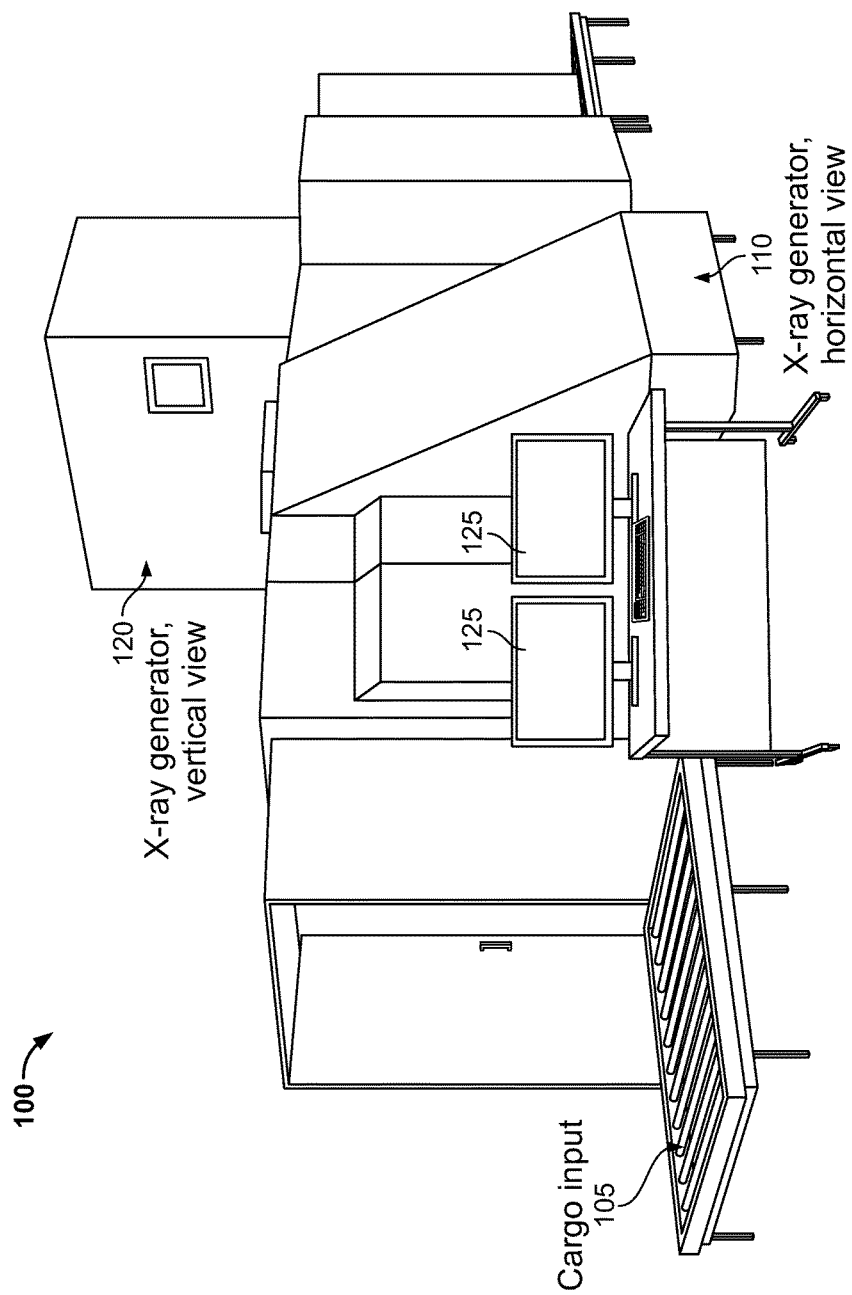
FIG. 1 is an illustration of an exemplary X-ray scanning system in accordance with an embodiment of the present specification.

FIG. 1 is an illustration of an exemplary X-ray scanning system in accordance with an embodiment of the present specification. Referring to FIG. 1, in an embodiment, cargo inspection system 100 uses a dual view mode of scanning. In an embodiment, system 100 comprises a first X-ray source 110 and a second X-ray source 120 that deliver images from two views, horizontal and vertical, respectively, which is described in greater detail below with respect to FIGS. 8a and 8b. This allows the system to produce two separate simultaneous images from approximately perpendicular orientations, thereby providing more comprehensive imagery, reducing the need for repositioning and rescanning and enabling rapid and accurate threat detection. In an embodiment, both X-ray sources are of same type and have the same operating voltage, which in an embodiment is in the range of 200 kV. In another embodiment, the inspection system uses a higher number of X-ray sources, such as three to five X-ray sources, each operating at a single voltage. In another embodiment, the X-ray source employed in the scanning system switches between two operating voltages in an interlaced fashion. In an embodiment of the present specification, each view corresponding to an X-ray source is supported by an L-shaped array of dual-energy detectors that separate the received X-ray radiation into at least two categories based on the energy contained in the X-ray spectra. In an embodiment, the dual energy detectors classify radiation with an energy level higher than a predefined threshold energy level as high energy X-rays and radiation with an energy level lower than the predefined threshold energy level as lower energy X-rays. Thus, the X-rays are parsed into a first energy bin and a second energy bin, wherein, in an embodiment, the first energy bin is low energy and the second energy bin is high energy.

In an embodiment, each detector array comprises two rows or sets of detectors, with the first set configured for detecting the low-energy X-rays and the second set configured for detecting the high-energy x-rays. While the embodiment described herein is a preferred embodiment, it should be noted herein that the present invention may include high energy detectors and low energy detectors dispersed within a detector array in any pattern, such as, but not limited to checkerboard, alternating, and/or mask, filter or attenuation-based systems, etc. This dual-energy data is acts as the foundation for generating the atomic number (Z) information, thereby providing material discrimination capabilities to the scanning system. The availability of material discrimination capability in the scanning system is valuable to the advanced image processing using the detection algorithms which are disclosed in the subsequent sections of the present specification.

In an embodiment, the operating voltage of the X-ray sources employed in the scanning system ranges between 1 kV to 1 MeV, and can be varied depending upon the system in which the present specification is implemented. Further, while the present embodiment describes a system that utilizes an X-ray source operating at a single voltage, it may be appreciated that an X-ray source that switches among two or more operating voltages can be used in other embodiments. Further, while the present embodiment describes a dual-view system, it may be appreciated that a single-view or multi-view system may be used as well.

Referring back to FIG. 1, a cargo input 105 comprises a conveyer mechanism to transfer cargo to be scanned inside the system 100. The dual energy data generated by respective detector arrays is processed by a processing unit to generate images of the cargo, which can be viewed on operator consoles 125. In accordance with the present specification, the processing unit can be a general purpose computing device and typically comprises an operating system, a memory device and a processor as would be appreciated by a person of skill in the art.

In an embodiment, the processor contained in the scanning system 100 of FIG. 1, comprises a software or computer application which is configured to implement or execute the various steps of the image processing technique/method disclosed herein. In an embodiment, the processor used for advanced image processing methods of the present specification is a part of the scanning system. In an alternate embodiment, the scanning system is provided access to a remote server comprising a processing unit for advanced image processing in accordance with the methods of the present specification. In addition, one of ordinary skill in the art would appreciate that the features described in the present application can operate on any computing platform including, but not limited to: a laptop or tablet computer; personal computer; personal data assistant; cell phone; server; embedded processor; digital signal processor (DSP) chip or specialized imaging device capable of executing programmatic instructions or code.

It should further be appreciated that the platform provides the functions described in the present specification by executing a plurality of programmatic instructions, which are stored in one or more non-volatile memories, using one or more processors and presents and/or receives data through transceivers in data communication with one or more wired or wireless networks.

In an embodiment, the system described in the FIG. 1 comprises multiple computing devices such that each computing device comprises wireless and wired receivers and transmitters capable of sending and transmitting data, at least one processor capable of processing programmatic instructions, memory capable of storing programmatic instructions, and software comprised of a plurality of programmatic instructions for performing the processes described herein. Additionally, the programmatic code can be compiled (either pre-compiled or compiled "just-in-time") into a single application executing on a single computer, or distributed among several different computers operating locally or remotely to each other.

In an embodiment, the data representative of the radiographic image is loaded from a memory device, which in an embodiment includes RAM, ROM, RAID array, flash drive, USB device, hard disk or other memory, to a processor that processes the data with the help of a computer program which includes instructions for performing various image processing functions on the data as described in subsequent sections of the present specification. In addition, those of ordinary skill in the art will recognize that devices of a less general purpose nature, such as hardwired devices, field programmable gate arrays (FPGAs), application specific integrated circuits (ASICs), or the like, can also be used for processing the images without departing from the scope and spirit of the present specification.

Figure 8A:
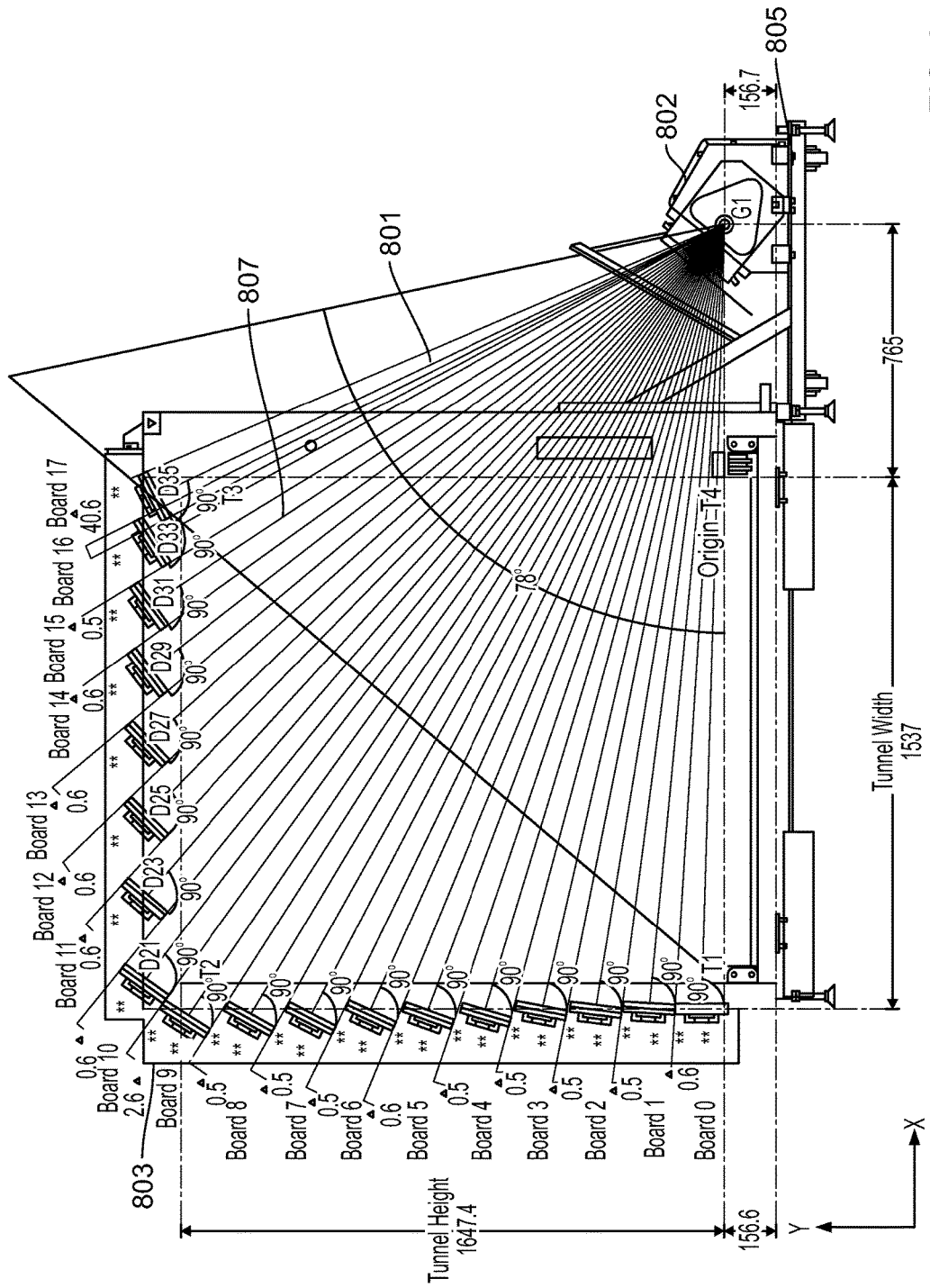
FIG. 8a illustrates a horizontal view scanning mode according to an embodiment of the present specification; and, FIG. 8b illustrates a vertical view scanning mode according to an embodiment of the present specification.
Figure 8B:
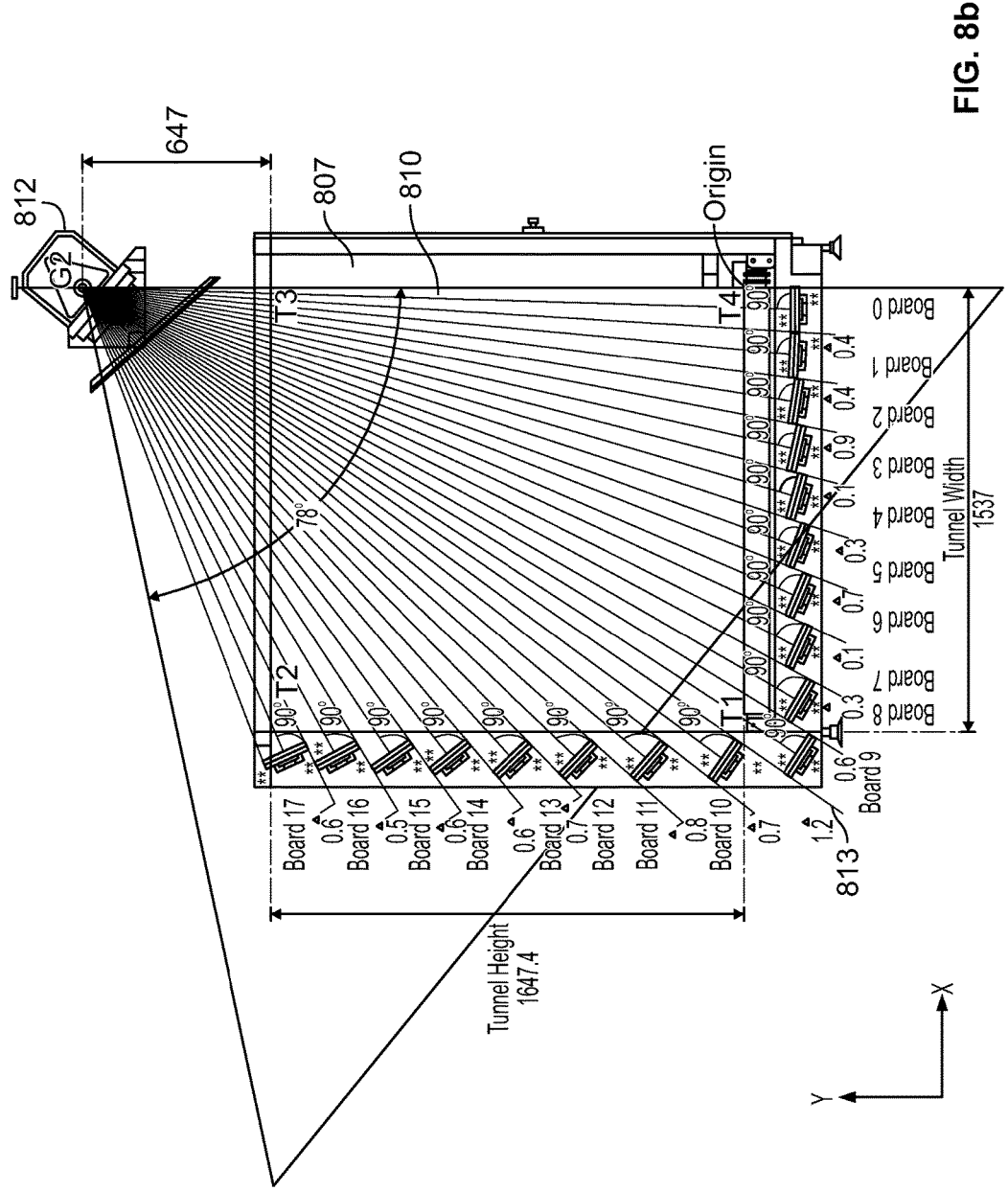

FIGS. 8a and 8b illustrate horizontal and vertical scanning modes, respectively, of the dual view inspection system in accordance with an embodiment of the present specification. As described in the embodiment shown in FIG. 1, the system produces two separate, but almost simultaneous images from two X-ray sources to provide a horizontal view and a vertical view of the cargo being scanned. In an embodiment, the first X-ray source is positioned in an approximately perpendicular direction to the second X-ray source, and therefore the two simultaneous images are produced from approximately perpendicular orientations. In an embodiment, the two separate images are produced within a couple of seconds of each other.

FIG. 8a is an illustration of an exemplary horizontal view scan mode. In an embodiment, a beam of X-rays is generated from source 802, which is positioned at the base of gantry 805 and configured such that, upon initial projection, X-rays are projected in a horizontal fan beam 801 parallel to ground level (in the xy-plane) through a scanning volume or tunnel 807. Horizontal X-ray source 802 is shown as X-ray source 110 in FIG. 1. In an embodiment, the angle of a projected fan beam is approximately 78 degrees. Transmitted X-rays are detected by an L-shaped array 803 of dual-energy detectors to generate a horizontal view of the object being scanned.

Referring to FIG. 8b, an exemplary vertical view scan mode is illustrated. In an embodiment, a beam of X-rays is generated from source 812, which is positioned at a distance above a scanning volume or tunnel 807 and configured such that, upon initial projection, X-rays are projected in a vertical fan beam 810 substantially perpendicular to ground level (in the yz-plane). Vertical X-ray source 812 is shown as X-ray source 120 in FIG. 1. In an embodiment, the angle of the projected fan beam is approximately 78 degrees. Transmitted X-rays are detected by an L-shaped array 813 of dual-energy detectors to generate a vertical view of the object being scanned.

Referring to FIGS. 8a and 8b together, it may be appreciated that the two X-ray sources 802 and 812 are approximately orthogonal to each other, and hence the two images produced provide perpendicular views. It should be noted herein that while FIGS. 8a and 8b represent exemplary layouts for the system of the present specification, the actual layouts and relative positions of the source/detector may change depending upon the footprint of the scanning system and scanning requirements.

Figure 3:
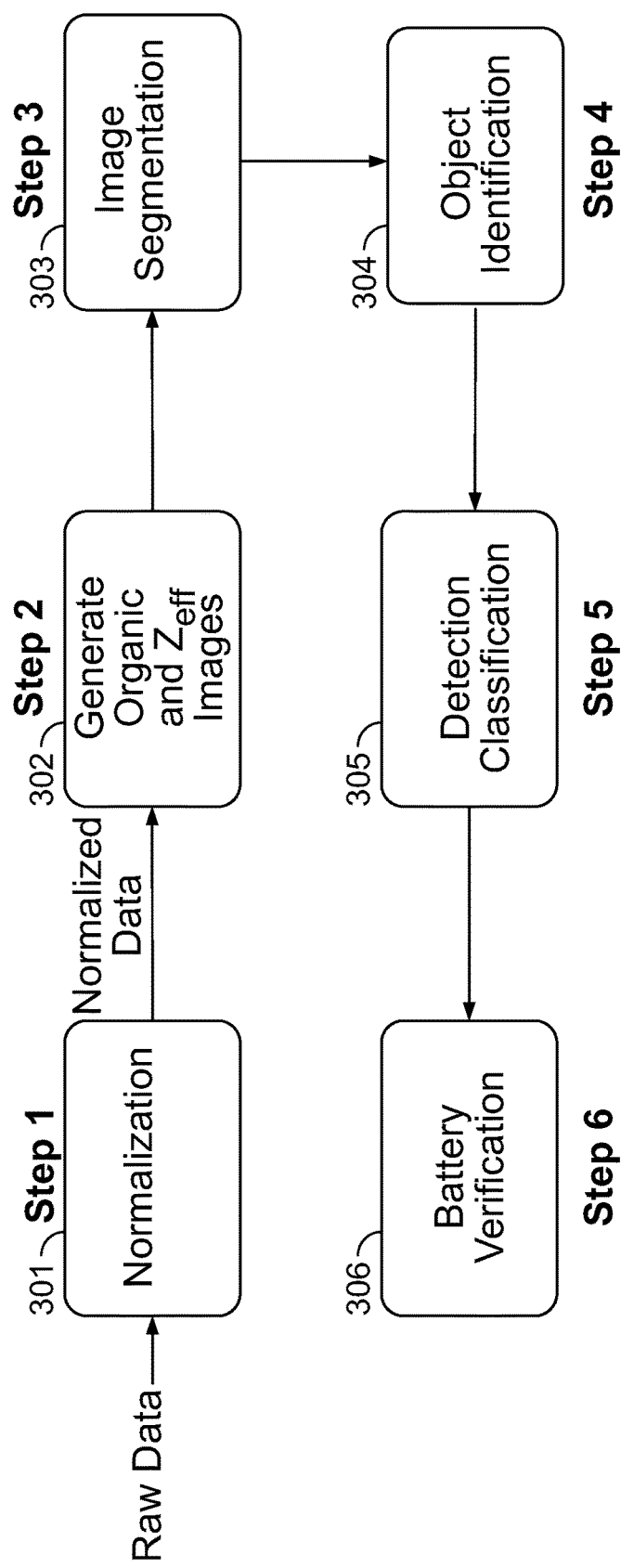
FIG. 3 is a flowchart illustrating a lithium battery detection method according to an embodiment of the present specification.

FIG. 3 is a flowchart illustrating a method of detection of lithium batteries in cargo, according to an embodiment of the present specification. The method disclosed in the present specification provides an advanced image processing technique which is used to process the detection data captured by a scanning system such as the scanning system disclosed in FIG. 1. Referring to FIG. 3, step 301 involves normalization of raw data that is obtained from an inspection system such as the inspection system disclosed in FIG. 1. The raw data is normalized to remove the effects of dark current, which is the signal measured in the absence of any X-rays. In addition, the normalization also removes the effects of pixel-to-pixel variation in the white field image, which is the image that is measured with the X-ray source on, but without an object in the direct path of the beam. The normalization process is performed on all transmission X-ray data before the image is displayed or further processed. In an embodiment, both the high-energy and low-energy X-ray transmission data captured by the inspection system is normalized before further processing. One of ordinary skill in the art would appreciate that various methods and techniques are known in the art to remove the effects of dark current and pixel-to-pixel variation in images and one can employ any of such methods without departing from the spirit and scope of the present specification.

In step 302, the resultant normalized data is used to generate organic and $Z_{eff}$ images. Using the normalized high-energy and low-energy X-ray transmission data effective atomic number ($Z_{eff}$) and organic images are computed for both the vertical and horizontal views of the scanned object. These computations involve mathematical approximations utilizing dual-energy images of polyethylene, aluminum, and steel objects of various thicknesses.

An atomic number map of the X-ray image is referred to as the "Z image", as is known in the art. Typically, the atomic number map represents an average atomic number of materials present in a specific region as since many objects encountered or detected during cargo inspection are compounds or mixtures of materials. In the present specification, the term "effective-Z image", or "$Z_{eff}$ image" is used to refer to a pixel-by-pixel map of effective atomic numbers of materials present in the corresponding regions in the X-ray radiograph. In an embodiment, the $Z_{eff}$ information derived from the dual-energy image is used in conjunction with a color map to assign different colors to different materials in the radiographic image. Thus, for example, in an embodiment, the low-Z materials such as plastics and other organic materials are represented by an orange color; high-Z materials such as steel and other inorganic materials are represented in a blue color; and medium-Z materials such as aluminum are indicated in a green color. In other embodiments of the present specification, different combinations of color codes are used.

Figure 2:
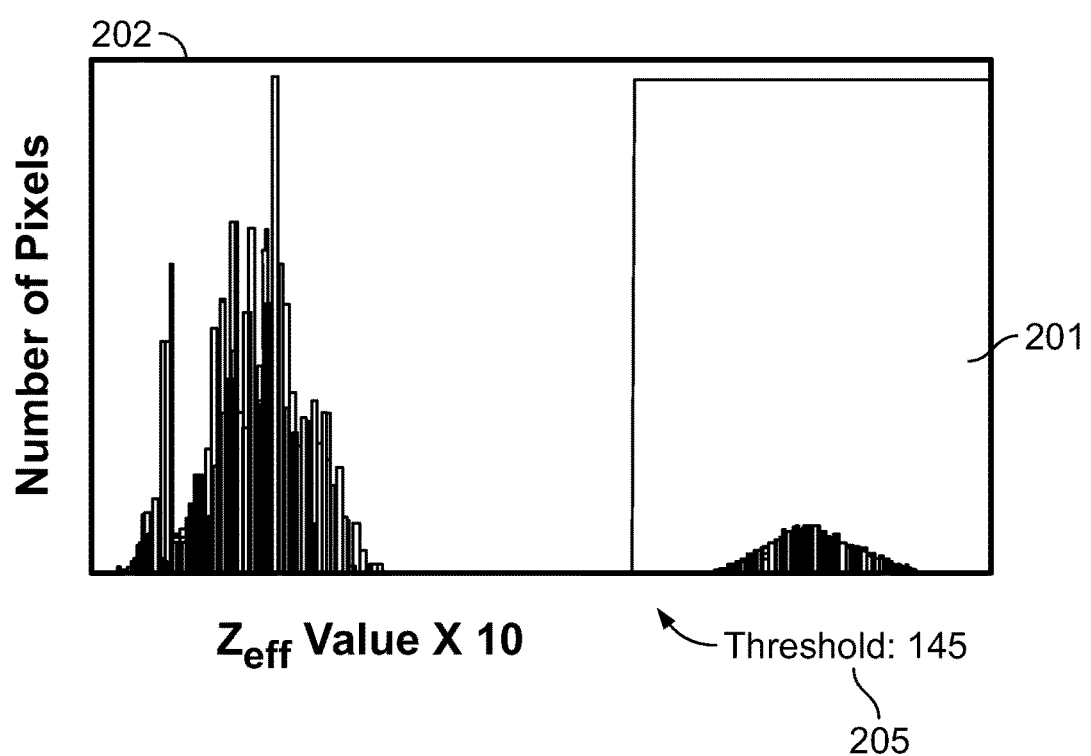
FIG. 2 is a histogram illustrating the distribution of $Z_{eff}$ values in a $Z_{eff}$ image in accordance with an embodiment of the present specification.

Further, in an embodiment, the distribution of $Z_{eff}$ values in a $Z_{eff}$ image is graphically represented by a histogram, as shown in FIG. 2. Referring to FIG. 2, the horizontal axis 201 in the graph represents the range of $Z_{eff}$ numbers and the vertical axis 202 represents the number of pixels present in the image corresponding to a particular $Z_{eff}$ number. For easier representation of data, the $Z_{eff}$ values on the horizontal axis are multiplied by a factor of 10. In an embodiment, a threshold value of $Z_{eff}$, represented as 205, is used in the histogram to clearly distinguish low atomic number materials from high atomic number materials present in the scanned region. In an embodiment, the threshold value of $Z_{eff}$ is chosen as 14.5 (normalized as 145 in the histogram for easier representation of data) which allows the system to distinguish high-Z materials such as Li batteries from the low-Z materials present in the cargo.

Figure 4A:
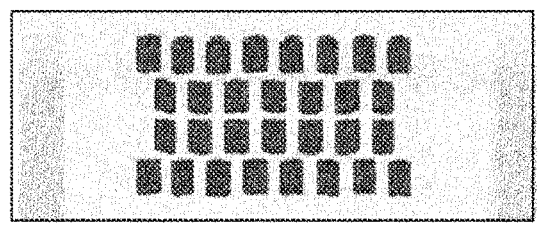
FIG. 4a is a top view of a radiographic image generated when the method of present specification is applied to bare batteries, according to an embodiment.
Figure 4B:
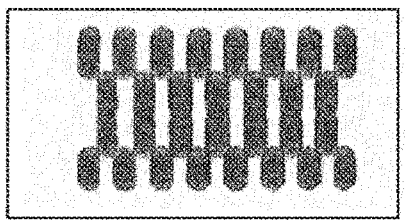
FIG. 4b is a side view illustration of a radiographic image generated when the method of present specification is applied to bare batteries according to an embodiment.

In an embodiment, the threshold value of $Z_{eff}$ is predetermined through the $Z_{eff}$ measurements of Li batteries obtained from bare battery images, such as those shown in FIG. 4A and FIG. 4B. Bare batteries images are images of batteries in the absence of any clutter, such that their images provide the low-end limit of the $Z_{eff}$ range for Li batteries. It may be appreciated that an image of a Li battery in the presence of any clutter will have a $Z_{eff}$ value greater than the $Z_{eff}$ value associated with an image of a bare Li battery which is placed without any surrounding clutter. This lower-end limit represents a threshold atomic number for lithium batteries, and any image pixel with a $Z_{eff}$ lower than this threshold is not indicative of the presence of a Li battery.

It is also known in the art that a pixel-by-pixel map of the "organic density" of materials in a region is known as its organic image. Organic density is a measure of the amount of organic content in a material and is defined as the equivalent polyethylene thickness in a material multiplied by a constant. For example, steel has no organic content; therefore its equivalent organic thickness is very low and, consequently, its organic density value is close to zero. Analyzing the organic image is an effective way to remove metal clutter in an X-ray image, thereby eliminating regions that may cause false alarms in the detection algorithm. In an embodiment of the present specification, the processing unit present in the scanning system utilizes the normalized data generated in step 301 to generate such organic image of the scanned material for both top view and side view.

It is also known in the art that pixel-by-pixel maps of the attenuation of high-energy and low-energy X-rays are utilized to segment certain regions of the X-ray image. Pixel-by-pixel maps resulting from combining mathematically, which includes, but is not limited to adding or subtracting, these distinct these high- and low-energy attenuation values provides an additional method of identifying objects for classification.

Referring back to FIG. 3, in step 303, image segmentation is performed. In this process, a combination of thresholding, morphological image operations, and region-growing techniques are employed to segment $Z_{eff}$, organic, and attenuation-based images into regions that may possibly contain lithium batteries. It may be noted that thresholding is a method of image segmentation whereby all image pixels at or above a given value, known as the threshold, are grouped into regions that are similar according to predefined criteria. Image pixels below the threshold are also grouped into regions that are similar according to some other predefined criteria. Morphological image operations refer to a type of image processing in which the spatial form or structure of objects within the image is modified based on shape characteristics. Region-growing segmentation partitions an image into regions based on examining neighboring pixels of an initial set of "seed" pixels; from these "seeds", regions are grown by appending to each seed those neighboring pixels that have similar properties such as gray level, texture, and color. In an embodiment, thresholding is used to identify the initial set of seed pixels within an image map.

In an embodiment, threshold-based segmentation is applied on the $Z_{eff}$ image. It may be noted that the result of this process of image segmentation depends on the degree of clutter, the type of cargo present, and superposition of cargo and batteries. Thus, not all segmented regions may actually represent batteries and an accurate determination of batteries would require further processing and analysis. However, the present step is important as its accuracy may determine which suspect regions will be investigated further in the later steps. Genuine regions overlooked during segmentation may not be investigated again, which would result in a lower probability of detection. On the other hand, when a large number of benign regions are retained after segmentation, the computation time for later steps of the algorithm is increased and there may also be a higher probability of false alarms.

In an embodiment, the present specification describes the use of two segmentation approaches. The first approach uses thresholding of the $Z_{eff}$ image to extract regions within the image that could be Li batteries. The second approach employs region-growing based segmentation of the organic image to reveal regions that could be Li batteries. It may be noted that the two segmentation approaches have their strengths and weaknesses, and the application of either or both may be warranted for a particular application. For example, thresholding the $Z_{eff}$ image may work for low-Z and some low-clutter cargoes, however, its application in high-Z and high-clutter cargoes may result in a highly-cluttered segmented image that makes it difficult to differentiate benign regions from those that contain Li batteries, as shown and described with respect to in FIGS. 6c, 7c and 7d below. In such cases, in an embodiment, region-growing based segmentation of the organic image is used to reduce clutter, thereby lowering the number of regions of interest that need to be examined for batteries, as shown in FIGS. 6f, 7e and 7f below.

In an embodiment of the present specification, the Li battery detection algorithm implemented in the scanning system automatically determines which segmentation approach to apply, based on the examination of the $Z_{eff}$ histogram and the degree of clutter in the $Z_{eff}$ image. Thus for example, in an embodiment, thresholding of the $Z_{eff}$ image is employed when $Z_{eff}$ values exist in the range of atomic numbers corresponding to that of Li batteries for a low-clutter image. On the other hand, in an embodiment, in the absence of $Z_{eff}$ values within the range of atomic numbers corresponding to that of Li batteries the scanning system performs a region-growing segmentation process on the organic image.

In step 304, the resultant segmented image obtained in step 303 is subjected to the process of object identification. In this step, critical characteristics such as area, organic thickness, $Z_{eff}$ number, and other properties such as distance to the neighboring regions and shape similarity to the neighboring regions, are used to extract all possible regions of interest from the segmented image. In an embodiment, regions that pass predefined criteria, such as comprising a minimum area, are retained for further analysis in the next step, while the other regions are discarded.

In step 305, the resultant regions shortlisted in step 304 are subjected to a process of object classification. In an embodiment, the object classification process involves classifying the shortlisted regions within the images as those containing lithium batteries or those containing other objects. It may be noted that object identification process involves examining each pixel of a given image based on the predefined criteria, such as $Z_{eff}$ number range, organic density range, and their gradient range, to determine if the inspected pixel belongs to an old region or whether it should form a new region. The object classification step is performed after the process of object identification, and it involves inspecting all the identified objects (regions) and making new judgments based on the features extracted from each object. In an embodiment, the features examined in the process of object classification include area of a marked region, its organic intensity, $Z_{eff}$ number, shape, X-ray attenuation, a specific spatial arrangement comprising repeated regions (with similar characteristics) positioned in the form of an array (indicative of batteries packed in a the form of an array with space between them) and texture. Based on these features, the objects are classified either as lithium batteries or as other objects.

In an embodiment, an area (as measured in pixels) is indicative of a single lithium battery if it is of a size within the range of lithium batteries specified for detection. In an embodiment, the range of lithium batteries includes those on the order of 4000 pixels in size or greater, which represents lithium batteries used in power tools, motorized bicycles, and uninterruptible power supplies. Variations in image magnification due to the location of the object within the X-ray beam are accounted for in the calculation of object size.

In addition, due to the many ways that lithium batteries can be assembled and packaged, the $Z_{eff}$ values indicative of a lithium battery can vary, but are typically in the range of $Z_{eff}=14$ to $Z_{eff}=20$.

In an embodiment, batteries that are packed for bulk transport, such as typical D-size or C-size batteries, and laptop computer batteries, appear spatially arranged in substantially uniform arrays within an X-ray image. The actual spacing between these uniformly-spaced batteries can vary from approximately 1 cm to a few inches. In addition, very small lithium batteries, such as typical AA-size or AAA-size batteries, can be packaged side-by-side with no spacing between them. In these cases, texture analysis can be used to identify these tightly-packed batteries.

In an optional embodiment, the spatial arrangement is defined as a first rectangular portion having a $Z_{eff}$ in a range of 14 to 20, organic density (represented as a pixel map) on the order of 4000 pixels or greater, next to a second rectangular portion having a $Z_{eff}$ in a range of 14 to 20, organic density (represented as a pixel map) on the order of 4000 pixels or greater, and separated by a gap having a $Z_{eff}$ of less than 14. Thus, it should be noted that there can be any number of rectangular regions in a row that meet these characteristics, depending upon the size and type of battery.

In another embodiment, the features or evaluation parameters used in the object identification and classification stages of the method of present specification (as detailed with reference to FIG. 3) are combined to help identify the target objects. This approach is especially useful for cargoes with a combination of metal clutter and large amounts of organic material.

In another embodiment, additional image processing steps are performed to improve the segmented image. In an embodiment, such image processing steps include for example, morphological image operations to fill voids after segmentation, or to reduce clutter by removing extraneous remnants in the segmented image. In an embodiment, such image processing steps also include processing of X-ray attenuation values produced from the signals measured independently by the low- and high-energy (dual-energy) detectors.

In an embodiment, the above process depicted in FIG. 3 is completely automated by means of a processing unit associated with the dual-energy scanning system of FIG. 1. One of ordinary skill in the art would also appreciate that the present method of detection of lithium batteries may be applied to any kind of X-ray scanning and inspection system, and is not limited to dual energy systems. Further, the present method can be employed to detect lithium batteries in any kind of object, luggage, container or cargo. In an embodiment, the process depicted in FIG. 3 optionally includes a step 306 which involves actual verification of regions which are supposed to contain lithium batteries as detected in the step 305. This step is performed for reviewing the results of the previous steps and for fine-tuning the detection algorithm. In this step, regions classified as containing Li batteries are compared against the actual material (by manual search). Based on the accuracy of detection, classification parameters are revised and fine-tuned as needed.

FIGS. 4a-4f illustrate exemplary results of the detection method of present specification when used for scanning a box comprising only the lithium batteries in accordance with an embodiment. As shown in FIG. 4a and FIG. 4b, the top and side views of the box are shown as captured by a dual energy scanning system such as the scanning system shown in FIG. 1. The images are preferably color-coded depending on the effective Z of the material wherein the lithium batters are shown in a specific blue color as they have a $Z_{eff} \approx 15$ (which is higher than the threshold value of 14.5 employed during the scanning)

Figure 4C:
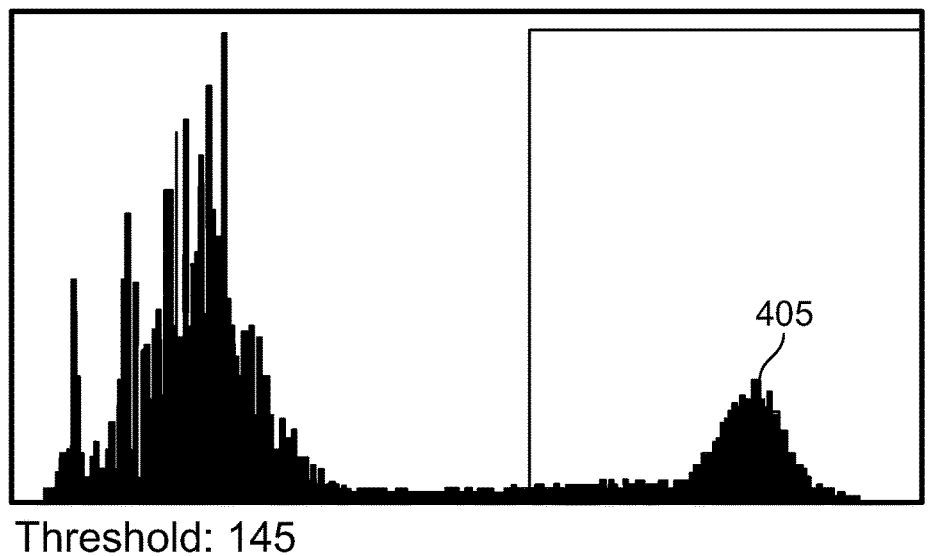
Figure 4D:
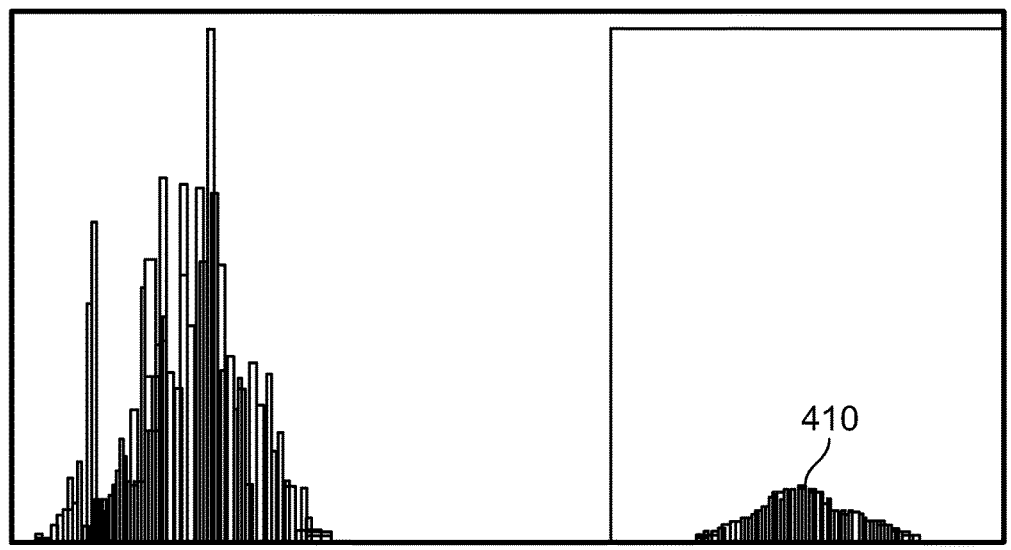
FIG. 4d illustrates the $Z_{eff}$ histogram corresponding to the image shown in FIG. 4b.
Figure 4E:
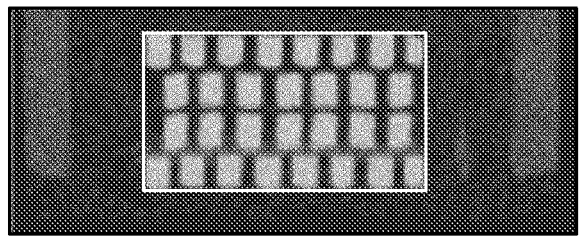
FIG. 4e is a top view illustration of a segmented $Z_{eff}$ image, according to an embodiment.
Figure 4F:
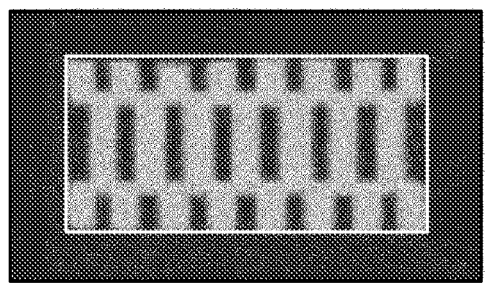
FIG. 4f is a side view illustration of a segmented $Z_{eff}$ image, according to an embodiment.

Referring to FIG. 4c and FIG. 4d, histograms for the top-view and side-view $Z_{eff}$ images are shown. Right-most peaks 405, 410 centered at approximately $Z_{eff}=18.3$ can be seen on both histograms; this value corresponds to the Li batteries in the $Z_{eff}$ image. It may be noted that number corresponding to the peak is slightly higher than the expected value of $Z_{eff}$ for lithium (15), due to the non-optimized parameters used to generate the $Z_{eff}$ image. When a lower-limit threshold of 145 (i.e., $Z_{eff}$=14.5) is applied, the cyan-colored battery regions are extracted. These extracted regions are shown in the segmented $Z_{eff}$ images in FIGS. 4e (top view) and 4f (side view). Although segmentation of the target object in X-ray images of bare batteries is very easy and straightforward, this simple step enables to establish a lower bound on the threshold value that is required for extracting Li batteries from cluttered cargo.

It may be noted that the same threshold value can be applied effectively to a variety of Li battery types. This is shown in FIGS. 5a-5f, which illustrate the exemplary results when the detection method of present specification was used for scanning different types of lithium batteries wherein a threshold $Z_{eff}$ value of 14.5 was used in all such analysis. In each of the FIGS. 5a-5f, the top image in each figure is the x-ray image of a sample and the bottom image is the corresponding segmented $Z_{eff}$ image for the same sample.

Referring to FIGS. 5a and 5b, the top-view and side-view images, respectively, for LSH14 Li-metal batteries are shown. In FIGS. 5c and 5d, the top-view and side-view images respectively, for 50-cycle electric bike Li-ion battery are shown. Referring to FIGS. 5e and 5f, the top-view and side-view images respectively, for BL1830 power tool Li-ion battery 510 and 6-cell laptop Li-ion battery 520 are shown. The results indicate that the same threshold, $Z_{eff}$=14.5, can be applied effectively to a variety of Li battery types.

Figure 6A:
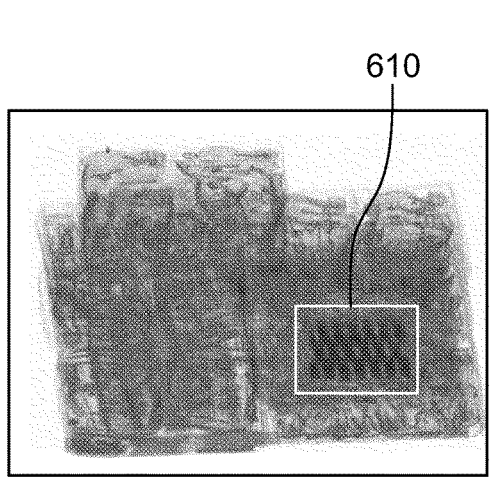
FIG. 6a depicts a top view of radiographic image that is generated when the method of present specification is applied to a moderately cluttered cargo, according to an embodiment.
Figure 6B:
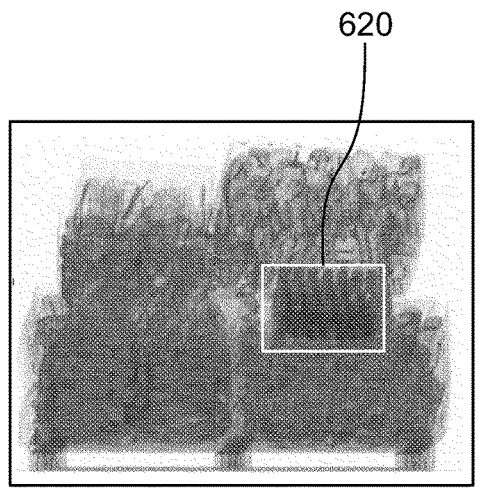
FIG. 6b depicts a side view of radiographic image that is generated when the method of present specification is applied to a moderately cluttered cargo, according to an embodiment.
Figure 6C:
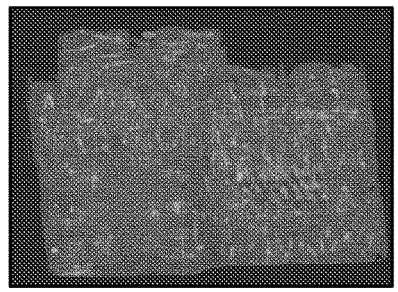
FIG. 6c illustrates a top view of segmented $Z_{eff}$ image that is generated when the method of present specification is applied to a moderately cluttered cargo according to an embodiment.
Figure 6D:
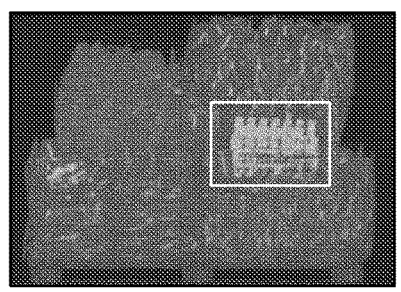
FIG. 6d illustrates a side view segmented $Z_{eff}$ image that is generated when the method of present specification is applied to a moderately cluttered cargo according to an embodiment.
Figure 6E:
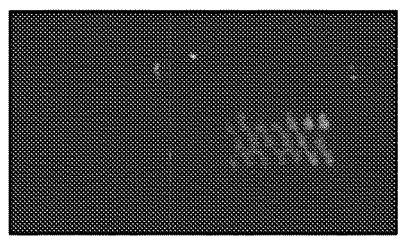
FIG. 6e illustrates a top view of an organic image that is generated when the method of present specification is applied to a moderately cluttered cargo according to an embodiment.
Figure 6F:
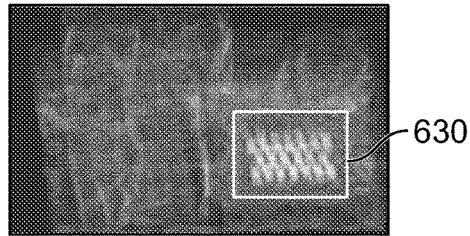
FIG. 6f illustrates the organic image shown in FIG. 6e with segmented battery areas, according to an embodiment.

FIGS. 6a-6f illustrate the exemplary results when the battery detection method of the present specification was used to scan a moderately cluttered cargo, according to an embodiment. Referring to FIGS. 6a and 6b respectively, top-view and side-view X-ray scan images of the cargo are shown. For the purpose of illustration, battery regions 610 and 620 are marked in the radiographic images. Segmented $Z_{eff}$ image of top view and bottom view are shown respectively in FIGS. 6c and 6d. The segmented images are obtained by applying a threshold of $Z_{eff}$=14.5 to the radiographic images, as explained earlier. However, thresholding the $Z_{eff}$ image does not always yield good segmentation results, as can be seen from FIG. 6c, where the presence of batteries is not revealed in the top view.

Therefore, in an embodiment, the segmentation result is improved by deploying a region-growing approach using the initial threshold image as seed to grow the partially-segmented battery regions. The region-growing algorithm is a technique consisting of two steps. In the first step, thresholding is used to identify seed pixels as an initial condition with an image map. In the second step, each seed is expanded recursively by examining all the immediate neighboring pixels based on pixel value and pixel gradient value to determine if a neighboring pixel belongs to the same region. In an embodiment, a region-growing based segmentation approach is applied on the top-view organic image, which is shown in FIG. 6e. FIG. 6f shows the resultant top-view image with segmented battery areas 630, where the region boundaries are outlined in blue. Thus, segmentation resulting from the region-growing approach is significantly improved.

It may be noted that thresholding the $Z_{eff}$ image results in extraction of all metallic regions, thereby making it difficult to differentiate the benign metals from Li batteries, especially in cargoes with high metallic clutter. On the other hand, segmentation of the organic image reduces the clutter significantly, thereby eliminating regions that may contribute to false alarms in later stages of the algorithm.

Figure 7A:
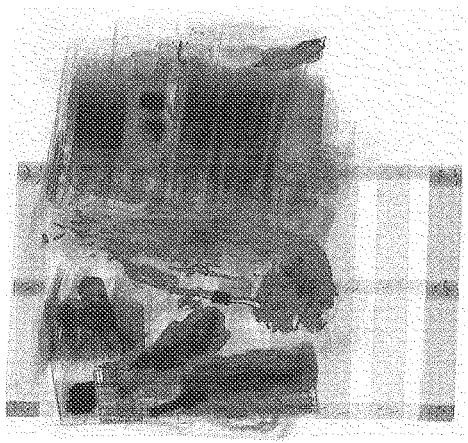
FIG. 7a depicts a top view of a radiographic image that is generated when the method of present specification is applied to a highly cluttered cargo, according to an embodiment.
Figure 7B:
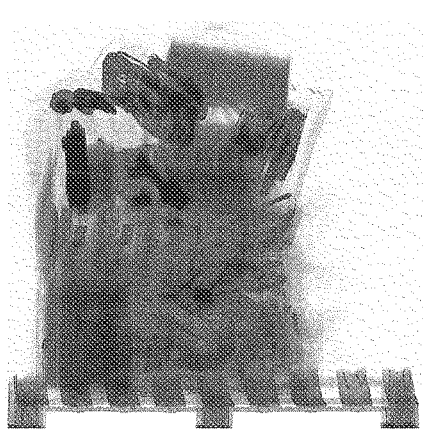
FIG. 7b depicts a side view of radiographic image generated when the method of present specification is applied to a highly cluttered cargo, according to an embodiment.
Figure 7C:
FIG. 7c illustrates a top view of segmented $Z_{eff}$ image that is generated when the method of present specification is applied to a highly cluttered cargo according to an embodiment.
Figure 7D:
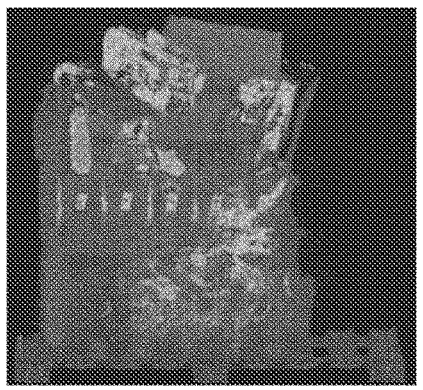
FIG. 7d illustrates a side view of segmented $Z_{eff}$ image that is generated when the method of present specification is applied to a highly cluttered cargo according to an embodiment.
Figure 7E:
FIG. 7e illustrates a top view of segmented organic image that is generated when the method of present specification is applied to a highly cluttered cargo according to an embodiment.
Figure 7F:
FIG. 7f illustrates a side view of segmented organic image that is generated when the method of present specification is applied to a highly cluttered cargo according to an embodiment.

FIGS. 7a-7f illustrates the exemplary results when the battery detection method of the present specification was used to scan high-clutter cargo, according to an embodiment. Referring to FIGS. 7a and 7b, top-view and side-view respectively, of the X-ray scan images of cargo, are shown. FIGS. 7c and 7d show the top-view and side-view respectively, of segmented $Z_{eff}$ images. Since the cargo has high metallic clutter, these images show several high-Z regions that are difficult to distinguish from Li batteries, if present. FIGS. 7e and 7f show the top-view and side-view respectively, of segmented organic images. As can be seen from these images, segmented organic images reduce the clutter and thus eliminate some regions that could cause false alarms.

One of ordinary skill in the art would appreciate that the calculations used to derive organic and $Z_{eff}$ images involve mathematical approximations using interpolation. As such, there may be some cases where, due to errors in the approximations, the image and thus the segmentation may be misleading. Therefore in an embodiment, instead of using a $Z_{eff}$ image, a combination of high-energy and low-energy images is used for analysis and computation. For example, the ratio of high-energy attenuation to low-energy attenuation values, and also the difference between these two values, is used for the purpose.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An inspection system for detecting the presence of lithium batteries, comprising:
   at least one radiation source;
   at least one detector array corresponding to the at least one radiation source; and,
   a processing unit comprising at least one processor, memory, and programmatic instructions, wherein, through the operation of the at least one processor, the memory, and the programmatic instructions, said processing unit:
   obtains transmission X-ray data representative of a generated radiographic image;
   normalizes said X-ray data to remove effects of dark current and to remove effects of pixel-to-pixel variations;
   generates at least one of organic image data and effective Z image data from said normalized data;
   segments said at least one of organic image data and effective Z image data based on an organic density of materials and a threshold effective atomic number ($Z_{eff}$), respectively;
   identifies at least one region of interest in said at least one of organic image data and effective Z image data based on said segmentation, wherein said at least one region of interest comprises a plurality of characteristics; and classifies said at least one region of interest as containing at least one lithium battery based on the plurality of characteristics of said at least one region of interest.

2. The inspection system of claim 1, wherein said at least one region of interest is identified in segmented images based on properties such as area, shape, organic thickness, and $Z_{eff}$ number.

3. The inspection system of claim 1, wherein the plurality of characteristics used by said processing unit to classify the at least one region of interest as containing at least one lithium battery include area, organic intensity, $Z_{eff}$ number, shape, X-ray attenuation level, spatial arrangement and texture of said region.

4. The inspection system of claim 1, wherein the processing unit classifies said at least one region of interest as containing at least two lithium batteries based on the plurality of characteristics of said at least one region of interest and wherein said plurality of characteristics include a spatial arrangement defined by a first rectangular portion having a $Z_{eff}$ in a range of 14 to 20 and an organic density represented by a pixel map of at least 4000 pixels, a second rectangular portion having a $Z_{eff}$ in a range of 14 to 20 and an organic density represented by a pixel map of at least 4000 pixels, and a gap separating the first rectangular portion and second rectangular portion, said gap having a $Z_{eff}$ of less than 14.

5. The inspection system of claim 1, wherein the system uses one X-ray source operating at a single voltage.

6. The inspection system of claim 1, wherein the system uses two X-ray sources, each operating at a single voltage.

7. The inspection system of claim 6, wherein the two X-ray sources switch between two operating voltages in an interlaced fashion.

8. The inspection system of claim 6, wherein a first X-ray source is approximately perpendicular to a second X-ray source.

9. The inspection system of claim 6 wherein, the inspection system produces two substantially simultaneous images from the two X-ray sources.

10. The inspection system of claim 9 wherein, the two simultaneous images provide a horizontal view and a vertical view of cargo being scanned.

11. The inspection system of claim 1, wherein the system uses from three to five X-ray sources, each operating at a single voltage.

12. The inspection system of claim 1, wherein the detector array comprises dual-energy detectors.

13. The inspection system of claim 1, wherein said threshold effective atomic number separates low-Z and high-Z materials in the effective Z image data.

14. The inspection system of claim 1, wherein during the segmentation of organic images, the processing unit applies region growing techniques.

15. The inspection system of claim 14, wherein said processing unit is configured to apply the region growing techniques when scanning cargo, baggage, or parcels with high clutter.

16. The inspection system of claim 1, wherein results of a scan are manually verified to fine-tune identification criteria for lithium batteries.

17. A method for detecting the presence of at least one lithium battery in a target in an inspection system comrising a processing unit, said method comprising:
 obtaining transmission X-ray data representative of a generated radiographic image of the target;
 normalizing said X-ray data to remove effects of at least one of dark current or pixel-to-pixel variation;
 generating effective Z images from said normalized data;
 segmenting said effective Z images based on a threshold effective atomic number ($Z_{eff}$);
 identifying at least one region of interest in said effective Z images based on said segmentation; and
 classifying said at least one region of interest as containing said at least one lithium battery based on characteristics of said at least one region of interest, said characteristics include a first substantially rectangular portion having a $Z_{eff}$ in a range of 14 to 20.

18. The method of claim 17 wherein the processing unit is configured to identify said at least one region of interest in segmented images based on properties such as area, shape, organic thickness, and $Z_{eff}$ number.

19. The method of claim 17 wherein the characteristics used for classifying at least one region of interest as containing at least one lithium battery further includes area, organic intensity, X-ray attenuation level, spatial arrangement and texture of said region.

20. The method of claim 17 wherein the characteristics used for classifying at least one region of interest as containing at least one lithium battery further includes a first substantially rectangular portion having a $Z_{eff}$ in a range of 14 to 20, a second substantially rectangular portion having a $Z_{eff}$ in a range of 14 to 20 and a gap separating the first substantially rectangular portion and second substantially rectangular portion, said gap having a $Z_{eff}$ of less than 14.

21. The method of claim 20 wherein an organic density of the first substantially rectangular portion is at least 4000 pixels and an organic density of the second substantially rectangular portion is at least 4000 pixels.

22. The method of claim 17, wherein the processing unit is adapted to use the threshold effective atomic number to separate low-Z and high-Z materials in the effective Z images.

23. The method of claim 17, wherein the processing unit is configured to apply region growing techniques when scanning cargo, baggage, or parcels with high clutter.

* * * * *